United States Patent [19]

Wang et al.

[11] Patent Number: 5,876,977

[45] Date of Patent: Mar. 2, 1999

[54] POLYMERASE CHAIN REACTION-RESTRICTION FRAGMENT LENGTH POLYMORPHISM TEST FOR THE AUTHENTICATION OF TRADITIONAL CHINESE MEDICINES

[75] Inventors: Jun Wang; Shaw Pang Chui; Paul Pui-Hay But; Ngan Fai Ngor Karenda, all of Shatin, Hong Kong

[73] Assignee: The Chinese University of Hong Kong, Hong Kong, Hong Kong

[21] Appl. No.: 778,912

[22] Filed: Jan. 3, 1997

[51] Int. Cl.⁶ .............................. C12Q 1/68; C12P 19/34; C07H 21/04; C12N 15/00
[52] U.S. Cl. ........................... 435/91.2; 435/6; 435/91.1; 536/23.1; 536/24.33; 935/31; 935/8; 935/27; 935/78
[58] Field of Search .............................. 435/6, 91.1, 91.2, 435/183; 536/23.1, 23.6, 24.3, 24.33; 935/77, 78

[56] References Cited

U.S. PATENT DOCUMENTS 4,965,188  10/1990  Mullis et al. ................................ 435/6

OTHER PUBLICATIONS

David M. Hillis and Michael T. Dixon, The Quarterly Review of Biology vol. 66 No. 4: 410–449, (1991).

Wen–Sheng Lang, et al., Journal of Chinese Pharmaceutical Sciences, pp. 133–143, (1993).

Jun Wen, et al., Molecular Phylogenetics And Evolution vol. 6, No. 2, pp. 167–177, Article No. 0069, (1996).

*Primary Examiner*—Bradley L. Sisson
*Attorney, Agent, or Firm*—Albert Wai-Kit Chan; Cooper & Dunham LLP

[57] ABSTRACT

This invention provides a procedure for authentication of plant and animal materials used as traditional Chinese medicine is described. This method amplifies and detects the discrete and species-specific RFLP patterns in the region of rDNA. The present invention offers a reliable and definite way to identify morphologically similar Chinese medicine, using a minute amount of biological samples. Its application in the authentication of American and Oriental ginsengs is illustrated in detail.

13 Claims, 11 Drawing Sheets

FIG. 1

```
ACTCGCCGTT ACTAGGGGAA TCCTTGTAAG TTTCTTTTCC TCCGCTTATT GATATGCTTA
AACTCAGCGG GTAGTCCCGC TGACCTGGGG TCGCGGTCGG AGCGCACGTC GAGGAGCGCA
ACAGGGTCAT GAGAGCTTTT GCTGGCGACG GGTCACCGCA CGACATGAGA AGAGGGCTTT
TTACAACCAC CACTTGTCGT GACGTCCATC GCCAAGGACT CGCATTTGGG CCAACCGCGC
GGTGAGACAC GGCAGGCCAT TATCCGCCCC TCCGCCTCGA CTCCCGCAAA GGAGTGATGG
GTTGGGGGGC GACGCGATGC GTGAACGCCC AGGCAGACGT GCCCTCGGCC TAATGGCTTC
GGGCGCAACT TGCGTTCAAA GACTCGATGG TTCACGGGAT TCTGTAATTC ACACCAAGTA
TCGCATTTCG CTACGTTCTT CATCGATGCG AGAGCCGAGA TATCCGTTGC CGAGAGTCGT
TTGTGTTTTA GAAAGACGCT TCCGCCGCCC GCAAACGGGG GGGACGCGTG CAGTTCAGTT
TGATTTCCTT GGCGCATTCC GCGCCGGGGG GTCGTTGTTC GGACGAGAGC CACCCAAGGG
TGGTCCCCGA CCATGGGTTT GCAACTTGGG GAGCTTGCGC ACCCCTCGTC CCTCACCCGG
TATTGTAACG TGTTCGCGGG TCGTTCTGCT ATGCAGGTTT CGACAATGAT CCTTCCGCAG
GTTCACCTAC GGAAACCTTG TTACGACTTC TCCTTCCTCT AAATGATAAG GTTCAGTGGA
CTTCTTTCGA CGTCGCGGGC AGCGAACCGC CCACGTCGCC GCAATCCGAA CACTTCACCG
GACCATTCAA TCGGTAGGAG CGACGGGCGG TGTG
```

FIG. 2A

```
ACTCGCCGTT ACTAGGGGAA TCCTTGTAAG TTTCTTTTCC TCCGCTTATT GATATGCTTA
AACTCAGCGG GTAGTCCCGC TGACCTGGGG TCGCGGTCGG AGCGCACGTC GAGGACGGCG
CAACAGGGTC ATGAGAGCTT TTGCTGGCGA CGGGTCACCG CACGACATGA GAAGAGGGCT
TTTTACAACC ACCACTTGTC GTGACGTCCA TCGCCAAGGA CTCGCATTTG GGCCAACCGC
GCGGTGAGAC ACGGGAGGCC ATTATCCGCC CCTCCGCCTC AACTCCCGCA AGGGAGTGAT
GGGTTGGGGG GCGACGCGAT GCGTGACGCC CAGGCAGACG TGCCCTCGGC CTAATGGCTT
CGGGCGCAAC TTGCGTTCAA AGACTCGATG GTTCACGGGA TTCTGCAATT CACACCAAGT
ATCGCATTTC GCTACGTTCT TCATCGATGC GAGACGCGAG ATATCCGTTG TCGAGAGTCG
TTTGTGTTTT AGAAAGACGC TTCCGCCGCC CGCAAACGGG GGGGACGCGT GCAGTTCAGT
TTGATTTCCT TGGCGCATTC CGCGCCGGGG GGTCGTTGTT CGGACGAGAT CCACCCAAGG
GTGGTCCCCG ACCATGGGTT TGCAACTTGG GGAGCTTGCG CACCCCTCGT CCCTCACCCG
GTATTGTAAC GTGTTCGCGG GTCGTTCTGC TATGCAGGTT TCGACAATGA TCCTTCCGCA
GGTTCACCTA CGGAAACCTT GTTACGACTT CTCCTTCCTC TAAATGATAA GGTTCAGTGG
ACTTCTTTCG ACGTCGCGGG CAGCGAACCG CCCACGTCGC CGCAATCCGA ACACTTCACC
GGACCATTCA ATCGGTAGGA GCGACGGGCG GTGTG
```

FIG. 2B-1

```
              10         20         30         40         50
G1.DNA    1 ACTCGCCGTT ACTAGGGGAA TCCTTGTAAG TTTCTTTTCC TCCGCTTATT   5
IC.DNA    1 ACTCGCCGTT ACTAGGGGAA TCCTTGTAAG TTTCTTTTCC TCCGCTTATT   5

60         70         80         90        100
G1.DNA   51 GATATGCTTA AACTCAGCGG GTAGTCCCGC -TGACCTGGG GTCGCGGTCG  10
IC.DNA   51 GATATGCTTA AACTCAGCGG GTAGTCCCGC CTGACCTGGG GTCGCGGTCG  10

110        120        130        140        150
G1.DNA  101 GAGCGCACGT CGAGGACGGC GCAACAGGGT CATGAGAGCT TTTGCTGGCG  15
IC.DNA  101 GAGCGCACGT CGAGGACGGC GCAACAGGGT CATGAGAGCT TTTGCNGGCG  15

160        170        180        190        200
G1.DNA  151 ACGGGTCACC GCACGACATG AGAAGAGGGC TTTTTACAAC CACCACTTGT  20
IC.DNA  151 ACGGGTCACC GCACGACATG AGAAGAGGGC TTTTTACAAC CACCACTTGT  20

210        220        230        240        250
G1.DNA  201 CGTGACGTCC ATCGCCAAGG ACTCGCATTT GGGCCAACCG CGCGGTGAGA  25
IC.DNA  201 CGTGACGTCC ATCGCCAAGG ACTCGCATTT GGGCCAACCG CGCGGTGAGA  25

260        270        280        290        300
G1.DNA  251 CACGGGAGGC CATTATCCGC CCCTCCGCCT CAACTCCCGC AAGGGAGTGA  30
IC.DNA  251 CACGGGAGGC CATTATCCGC CCCTCCGCCT CAACTCCCGC AAGGGAGTGA  30

310        320        330        340        350
G1.DNA  301 TGGGTTGGGG GGCGACGCGA TGCGGTGACGC CCAGGCAGAC GTGCCCTCGG  35
IC.DNA  301 TGGGTTGGGG GGCGACGCGA TGCGGTGACGC CCAGGCAGAC GTGCCCTCGG  35

360        370        380        390        400
G1.DNA  351 CCTAATGGCT TCGGGGCGCAA CTTGCGTTCA AAGACTCGAT GGTTCACGGG  40
IC.DNA  351 CCTAATGGCT TCGGGGCGCAA CTTGCGTTCA AAGACTCGAT GGTTCACGGG  40

410        420        430        440        450
G1.DNA  401 ATTCTGCAAT TCACACCAAG TATCGCATTT CGCTACGTTC TTCATGGATG  45
IC.DNA  401 ATTCTGCAAT TCACACCAAG TATCGCATTT CGCTACGTTC TTCATGGATG  45
```

FIG. 2B-2

| | | | | | | | | |
|---|---|---|---|---|---|---|---|---|
| | 460 | 470 | 480 | 490 | 500 | | | |
| G1.DNA | 451 CGAGAGCGGA | GATATCCGTT | GTCGAGAGTC | GTTTGTGTTT | TAGAAAGACG | 50 | | |
| IC.DNA | 451 CGAGAGCCGA | GATATCCGTT | GCCGAGAGTC | GTTTGTGTTT | TAGAAAGACG | 50 | | |
| | 510 | 520 | 530 | 540 | 550 | | | |
| G1.DNA | 501 CTTCCGCCGC | CCGCAAACGG | GGGGGACGCG | TGCAGTTCAG | TTTGATTTCC | 55 | | |
| IC.DNA | 501 CTTCCGCCGC | CCGCAAACGG | GGGGGACGCG | TGCAGTTCAG | TTTGATTTCC | 55 | | |
| | 560 | 570 | 580 | 590 | 600 | | | |
| G1.DNA | 551 TTGGCGCATT | CCGCGCCGGG | GGGTCGTTGT | TCGGACGAGA | TCCACCCAAG | 60 | | |
| IC.DNA | 551 TTGGCGCATT | CCGCGCCGGG | GGGTCGTTGT | TCGGACGAGA | TCCACCCAAG | 60 | | |
| | 610 | 620 | 630 | 640 | 650 | | | |
| G1.DNA | 601 GGTGGTCCCC | GACCATGGGT | TTGCAACTTG | GGGAGCTTGC | GCACCCCTCG | 65 | | |
| IC.DNA | 601 GGTGGTCCCC | GACCATGGGT | TTGCAACTTG | GGGAGCTTGC | GCACCCCTCG | 65 | | |
| | 660 | 670 | 680 | 690 | 700 | | | |
| G1.DNA | 651 TCCCTCACCC | GGTATTGTAA | CGTGTTCGCG | GGTCGTTCTG | CTATGCAGGT | 70 | | |
| IC.DNA | 651 TCCCTCACCC | GGTATTGTAA | CGTGTTCGCG | GGTCGTTCTG | CTATGCAGGT | 70 | | |
| | 710 | 720 | 730 | 740 | 750 | | | |
| G1.DNA | 701 TTCGACAATG | ATCCTTCCGC | AGGTTCACCT | ACGGAAAACCT | TGTTACGACT | 75 | | |
| IC.DNA | 701 TTCGACAATG | ATCCTTCCGC | AGGTTCACCT | ACGGAAAACCT | TGTTACGACT | 75 | | |
| | 760 | 770 | 780 | 790 | 800 | | | |
| G1.DNA | 751 TCTCCTTCCT | CTAAATGATA | AGGTTCAGTG | GACTTCTTTC | GACGTCGCGG | 80 | | |
| IC.DNA | 751 TCTCCTTCCT | CTAAATGATA | AGGTTCAGTG | GACTTCTTTC | GACGTCGCGA | 80 | | |
| | 810 | 820 | 830 | 840 | 850 | | | |
| G1.DNA | 801 GCAGCGAACC | GCCCACGTCG | CCGCAATCCG | AACACTTCAC | CGGACCATTC | 85 | | |
| IC.DNA | 801 GCAGCGAACC | GCCCACGTCG | CCGCAATCCG | AACACTTCAC | CGGACCATTC | 85 | | |
| | 860 | 870 | 880 | 890 | 900 | | | |
| G1.DNA | 851 AATCGGTAGG | AGCGACGGGC | GGTGTG..... | .......... | .......... | 90 | | |
| IC.DNA | 851 AATCGGTAGG | AGCGACGGGG | .......... | .......... | .......... | 90 | | |

FIG. 3

```
ACTCGCCGTT ACTAGGGGAA TCCTTGTAAG TTTCTTTTCC TCCGCTTATT GATATGCTTA
AACTCAGCGG GTAGTCCCGC CTGACCTGGG GTCGCGGTCG GAGCGCACGT CGAGGACGGC
GCAACAGGGT CATGAGAGCT TTTGTTGGCG AAGGGTCACC GCACGACATG AGAAGAGGGC
TTTTTACAAC CACCACTTGT CGTGACGTCC ATCGCCAAGC ACTCGCATTT GGGCCAACCG
CACGGTGAGA CACGGGAGGC CAATATCCGC CCCTCCGCCT CGACTCCCGC AAGGGAGTGA
TGGGTTGGGG GGCGACGCGA TGCGTGAACG CCCAGGCAGA CGTGCCCTCG GCCTAATGGC
TTAGGGCGCA ACTTGCGTTC AAAGACTCGA TGGTTCACGG GATTCTGCAA TTCACACCAA
GTATCGCATT TCGCTACGTT CTTCATCGAT GCGAGAGCCG AGATATCCGT TGCCGAGAGT
CGTTTGTGTT TTAGAAAGAC GCTTCCGCCG CCCGCAAATG GGGGGACGC GTGCAGTTCA
GTTTGATTTC CTTGGCACAT TCCGCGCCGG GGGGTCGTTG TTCGGACGAG ATCCACCAAG
GGTGTCCCCG ACCATGGGTT TGCAACTTGG GGAGCTTGCG CACGCCTCGT CCCTCACCCG
GTATTGTAAC GTGTTCACGG GTCGTTCTGC TATGCAGGTT TCGACAATGA TCCTTCCGCA
GGTTCACCTA CGGAAACCTT GTTACGACTT CTCCTTCCTC TAAATGATAA GGTTCAGTGG
ACTTCTTTCG ACGTCGCGGG CAGCGAACCG CCCACGTCGC CGCAATCCGA ACACTTCACC
GGACCATTCA ATCGGTAGGA GCGACGGGCG GTGTG
```

FIG. 4

```
ACTCGCCGTT ACTAGGGGAA TCCTTGTAAG TTTCTTTTCC TCCGCTTATT GATATGCTTA
AACTCAGCGG GTAGTCCCGC TGACCTGGGG TCGCGGTCGG AGCGCACGTC GAGGACGGCG
CAACAGGGTC ATGAGAGCTT TTGCTGGCGA CGGGTCACCG CACGACATGA GAAGAGGGCT
TTTTACAACC ACCACTTGTC GTGACGTCCA TCGCCAAGGA CTCGCATTTG GGCCAACCGC
GCGGTGAGAC ACGGGAGGCC ATTATCCGCC CCTCCGCCTC GACTCCCGCA AAGGAGTGAT
GGGTTGGGGG GCGACGCGAT GCGTGAACGC CCAGGCAGAC GTGCCCTCGG CCTAATGGCT
TCGGGCGCAA CTTGCGTTCA AAGACTCGAT GATTCACGGG ATTCTGCAAT TCACACCAAG
TATCGCATTT CGCTACGTTC TTCATCGATG CGAGAGCCGA GATATCCGTT GCCGAGAGTC
GTTTGTGTTT TAGAAAGACG CTTCCGCCGC CCGCAAACGG GGGGACGCG TGCAGTTCAG
TTTGATTTCC TTGGCGCATT CCGCGCCGGG GGTCGTTGT TCGGACGAGA GCCACCCAAG
GGTGGTCCCC GACCATGGGT TTGCAACTTG GGGAGCTTGC GCACCCCTCG TCCCTCACCC
GGTATTGTAA CGTGTTCGCG GGTCGTTCTG CTATGCAGGT TTCGACAATG ATCCTTCCGC
AGGTTCACCT ACGGAAACCT TGTTACGACT TCTCCTTCCT CTAAATGATA AGGTTCAGTG
GACTTCTTTC GACGTCGCAG GCAGCGAACC GCCCACGTCG CCGCAATCCG AACACTTCAC
CGGACCATTC AATCGGTAGG AGCGACGGGC GGTGTG
```

FIG. 5

```
ACTCGCCGTT ACTAGGGGAA TCCTTGTAAG TTTCTTTTCC TCCGCTTATT GATATGCTTA
AACTCAGCGG GTAGTCCCGC CTGACCTGGG GTCGCGGTCG GAGCGCGCGT CGGGGACGGC
GCAACAGGGT CGTGAGAGCC TTTGCCGGCG ACGGGTCACC GCACGACTTG AGAAGAGGGC
TTTTTACAAC CACCACTTGT CGTGACGTCC GTCGCCGAGG ACTCGCATTT GGGCCAACCG
CGCGGTTAGA CACGGGAGGC CAATATCCGC CCCTCCGCCT CGACTCCGT AAGGGAGTGA
TGGGTTGGGG GGCGACGCGA TGCGTGACGC CCAGGCAGAC GTGCCCTCGG CCTAATGGCT
TAGGGCGCAA CTTGCGTTCA AAGACTCGAT GGTTCACGGG ATTCTGCAAT TCACACCAAG
TATCGCATTT CGCTACGTTC TTCATCGATG CGAGAGCCGA GATATCCGTT GCCGAGAGTC
GTTTGTGTTT TAGAAAGACG CTTCCGCCGC CCGCAAACGG GGGGACGCG TGCAGTTCAG
TTTGATTTCC TTGGCGCATT CCGCGCCGGG GGTCGTTGT TCGGACGGGG AGCACCCGGG
GGCGGCCCCC GACCATGGGT TCGGAACTTG GGGGGCTTGC GCACCCTTCG TCCCTCACCC
GGTGTTGAAA CGTGTTCGCG GGTCGTTCTG CTGTGCAGGT TTCGACAATG ATCCTTCCGC
AGGTTCACCT ACGGAAACCT TGTTACGACT TCTCCTTCCT CTAAATGATA AGGTTCAGTG
GACTTCTTTC GACGTCGCGG CAGCGAACCG CCCACGTCGC CGCAATCCGA ACACTTCACC
GGACCATTCA ATCGGTAGGA GCGACGGGCG GTGTG
```

FIG. 6

5' AGCCATCCTCGCTGCCCGCCACAC 3'

3' ACTCGCCGTTACTAGGGGAA 5'

POLYMERASE CHAIN REACTION-RESTRICTION FRAGMENT LENGTH POLYMORPHISM TEST FOR THE AUTHENTICATION OF TRADITIONAL CHINESE MEDICINES

FIELD OF THE INVENTION

This invention is directed to the authentication of Chinese medicinal materials based upon RFLP patterns of the PCR-amplified rDNA.

BACKGROUND OF THE INVENTION

Traditional Chinese medicine refers to the medicinal materials and clinical application of such materials in the framework of the theoretical and empirical parameters cicumscribed by the Chinese people in the last 2–3 millennia. This medical system and many of the medicinal materials has spread to and adopted by other Oriental countries such as Japan and Korea and evolved into Oriental medicine in those countries. As a result, traditional Chinese medicine should not be limited to only the herbs and other natural products used in Chinese medicine, but also to Oriental medicine. Traditional Chinese medicine currently in mainland China also covers the practice and medicinal materials used by Tibetan, Mongolian and other ethnic minorities.

The herbs and other natural products (animals and minerals) used in Chinese medicine have been recorded in a) classical herbals, e.g. Bencao Gangmu (本草綱目) and Bencao Gangmu Shiyi (本草綱目拾遺) which recorded American ginseng (the two together contain about 2,500 items; b) pharmacopoeia, e.g. Pharmacopoeia of the People's Republic of China (中華人民共和國藥典) which contains some 600 items; and c) treaties, e.g. Encyclopedia of Chinese Materia Medica (Zhongyao Dacidian 中藥大詞典), which contain 5,767 items.

Traditionally the authentication of Chinese herbs relied upon morphological and histological inspection. In many cases, such as in the authentication of different ginseng species, and in the authentication of Acorus species, this method is unreliable. An effective program of authentication of Chinese herbs is essential and central issue in the healthy development of the herbal industry. It provides a necessary protection for consumers, minimises unfair business competition and prevents the health hazard of many adulterants.

In plant nuclear genome, genes for ribosomal RNA (rDNA) are normally clustered in an array of multiple tandemly repeated copies of the cistron of 18S-ITS1-5.8S-ITS2-28S (Hillis, D. M and Dixon, M. T., 1991, The Quarterly Review of Biology, 66: 411–453). The sequence separates the 18S and 5.8S rRNA genes is designated as ITS1 (Internal Transcribed Spacer 1) and the sequence between 5.8S and 28S is designated as ITS2. The coding regions of the three rDNA genes are highly conserved, whereas the sequence homology within the ITS1 and ITS2 regions are lower across the plant kingdom. Furthermore within a given individual organism or species, the rDNA sequence is usually very similar due to the homogenization of the sequence by gene conversion and crossing over. This invention takes advantage of these features of plant rDNA, and use PCR to amplify the DNA of ITS1-5.8S-ITS2 regions with the conserved DNA sequences flanking to the regions as primers, and explores the DNA polymorphism in different plant species within the ITS1-5.8S-ITS2 region as a means of authentication.

The roots of Panax quinquefolius (American Ginseng) and P. ginseng (Oriental ginseng) are important herbal medicinal materials widely applied in the Orient as tonic, prophylactic and anti-aging agents. In recent years the American ginseng, cultivated mainly in Wisconsin, USA, and British Colombia and Ontaria, Canada, enjoys increasingly popularity as a health food in Western countries. The ginseng trade is a big industry, in 1993 Hong Kong imports more than HK$1,500 million worth of American and Oriental ginsengs. The retail price of cultivated American ginseng is usually much more expensive than that of cultivated Oriental ginseng produced in China, and that prompts wild-spread practice of disguising Orient ginseng as American ginseng by dishonest merchants. Tremendous financial incentive is also responsible for the imitation or adulteration of ginsengs with some herbal products including several poisonous plants that bear morphological similarity with ginsengs. The two ginsengs also have different medical values and potency.

Both American and Oriental ginsengs, together with several important Chinese medicines including sanchi (P. notoginseng), belong to the genus of Panax in the family of Araliaceae. American ginseng and Oriental ginseng have similar morphological appearance. Furthermore many commercial ginseng products exist in the forms of powder or shredded slice, rendering their authentication by morphological and histological methods difficult and unpractical. In recent years, techniques have been developed to authenticate ginseng samples by examination of their ginsenoside profiles (Lang, Z., Lou, W S. and But, P P H, 1993, J. Clin. Pharm. Sci., 2:133–143). However, the application of chemical analysis may be limited as the amount of ginsenosides are significantly affected by many environmental factors such as the storage condition, the freshness of the products and the different post-harvest processing. In addition, the chemical method demands large quantity of materials for proper analysis.

SUMMARY OF THE INVENTION

This invention is based upon the DNA polymorphism in the ITS1-5.8S-ITS2 region of rDNA. Accordingly genomic DNA was isolated and the ITS regions of rDNA was selectively amplified using pairs of primers that correspond to the consensus DNA sequence within the rDNA. The resultant PCR products were then subject to the fragmentation by selected restriction endonuclease to generate, after electrophoresis, discrete and species-specific RFLP patterns. Application of this invention to authenticate American ginseng from Oriental ginseng and several common adulterants are detailed as examples.

BRIEF DESCRIPTION OF THE DRAWINGS

FIG. 1. ITS1-5.8S-ITS2 DNA sequence of P. quinquefolius (SEQ ID NO.2).

FIG. 2. (A). ITS1-5.8S-ITS2 DNA sequence of P. ginseng (SEQ ID NO.2). (B) G1 DNA is the same as the sequnece of P. ginseng; (SEQ ID NO.3) the IC DNA is the sequence from a Russian cultivar of P. ginseng. The four variables between the two are underlined (SEQ ID NO.4).

FIG. 3. ITS1-5.8S-ITS2 DNA sequence of P. japonicus (SEQ ID NO.5).

FIG. 4. ITS1-5.8S-ITS2 DNA sequence of P. notoginseng (SEQ ID NO.6).

FIG. 5. ITS1-5.8S-ITS2 DNA sequence of P. trifolium (SEQ ID NO.7). 5' AGCCATCCTCGCTGCCCGCCACAC 3' (SEQ ID NO.8) 3' ACTCGCCGTTACTAGGGGAA 5' (SEQ ID NO.9)

FIG. 6. The primers, 18d and 28cc, used to amplify ITS1-5.8S-ITS2 regions of the plant rDNA genes.

DETAILED DESCRIPTION OF THE INVENTION

Figure 7:
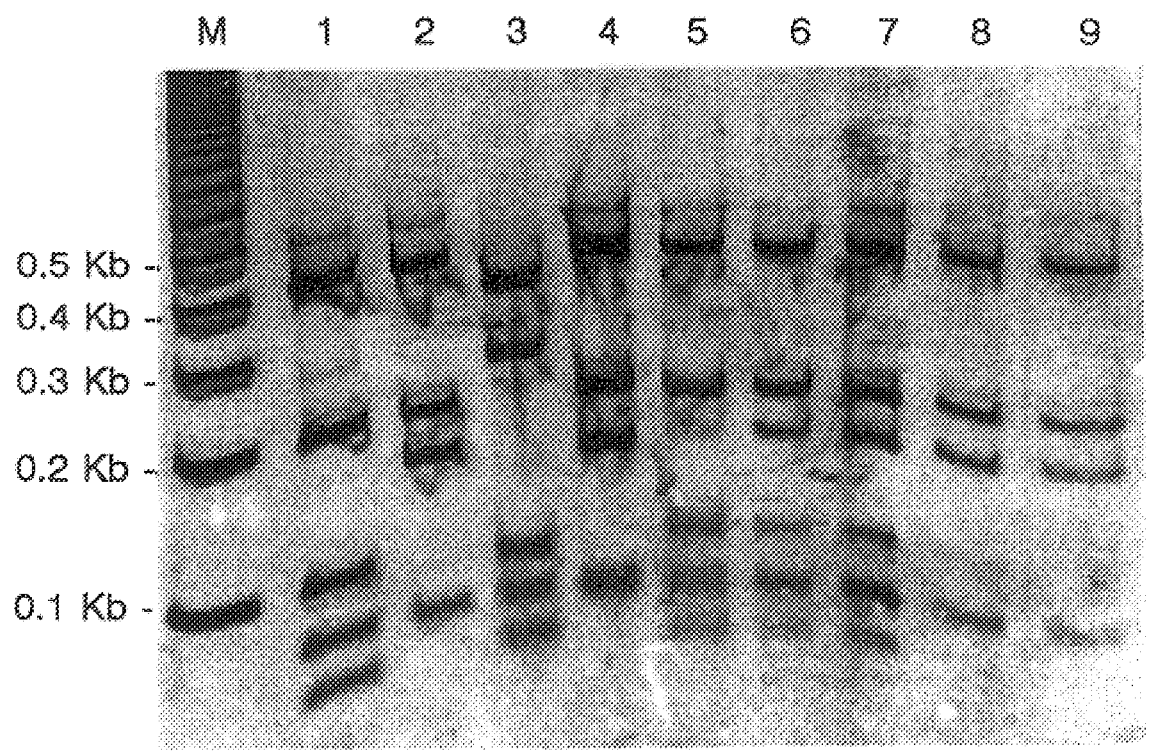
FIG. 7. The Hinf1 RFLP patterns of the ITS1-5.8S-ITS2 region for P. quinquefolius (American Ginseng), P. ginseng (Oriental ginseng) and their adulterants. Lane M, DNA size marker; lane 1, P. quinquefolius (American Ginseng); lane 2, P. ginseng (Oriental ginseng); lane 3, adulterant M. jalapa; lane 4, adulterant P. acinosa. Lane 5 to 9 represent the RFLP patterns of the mixed samples of American Ginseng and Oriental ginseng in different ratio. Lane 5, American Ginseng and Oriental ginseng in the ratio of 9:1; Lane 6, in the ratio of 7:3; Lane 7, in the ratio of 1:1; Lane 8, in the ratio of 3:7; and Lane 9, in the ration of 1:9. Two fragments of 0.1 kb and 0.06 kb present in American ginseng but are absent from Oriental ginsen, while a fragment of 0.17 kb present in Oriental ginseng but absent from American ginseng. M. jalapa contains two characteristic fragments of 0.4 kb and 0.3 kb in size. The plant DNA were extracted using CTAB (cetyl triethylammonium bromide) method as described in Experimental Details and their rDNA ITS regions were amplified by PCR using the primers specified in FIG. 6. The resultant PCR products were subject to restriction of Hinf1, fractionated on SDS-PAGE and silver stained.
Figure 8:
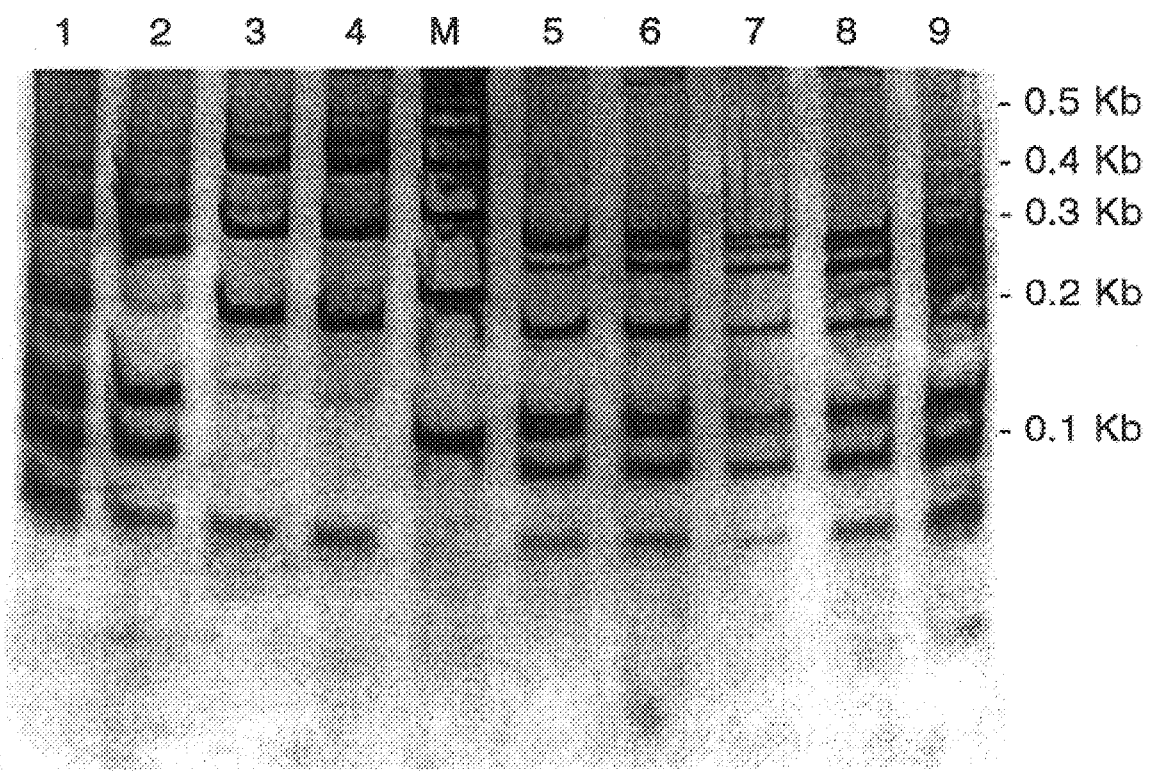
FIG. 8. The Taq1 RFLP patterns of the ITS1-5.8S-ITS2 region for P. quinquefolius (American Ginseng), P. ginseng (Oriental ginseng) and their adulterants. Lane M, DNA size marker; lane 1, P. quinquefolius (American Ginseng); lane 2, P. ginseng (Oriental ginseng); lane 3, adulterant M. jalapa; lane 4, adulterant P. acinosa. Lane 5 to 9 represent the RFLP patterns of the mixed samples of American Ginseng and Oriental ginseng in different ratio. Lane 5, American Ginseng and Oriental ginseng in the ratio of 9:1; Lane 6, in the ratio of 7:3; Lane 7, in the ratio of 1:1; Lane 8, in the ratio of 3:7; and Lane 9, in the ration of 1:9. A 0.18 kb fragment is present in American ginseng but absent from Oriental ginseng; while a 0.27 kb fragment is present in Oriental ginseng but absent from American ginseng. Both adulternats contains characteristic fragments of 0.28 kb and 0.4 kb in size. The plant DNA were extracted using CTAB method and their rDNA ITS regions were amplified by PCR using the primers specified in FIG. 6. The resultant PCR products were subject to restriction of Taq1, fractionated on SDS-PAGE and silver stained.
Figure 9:
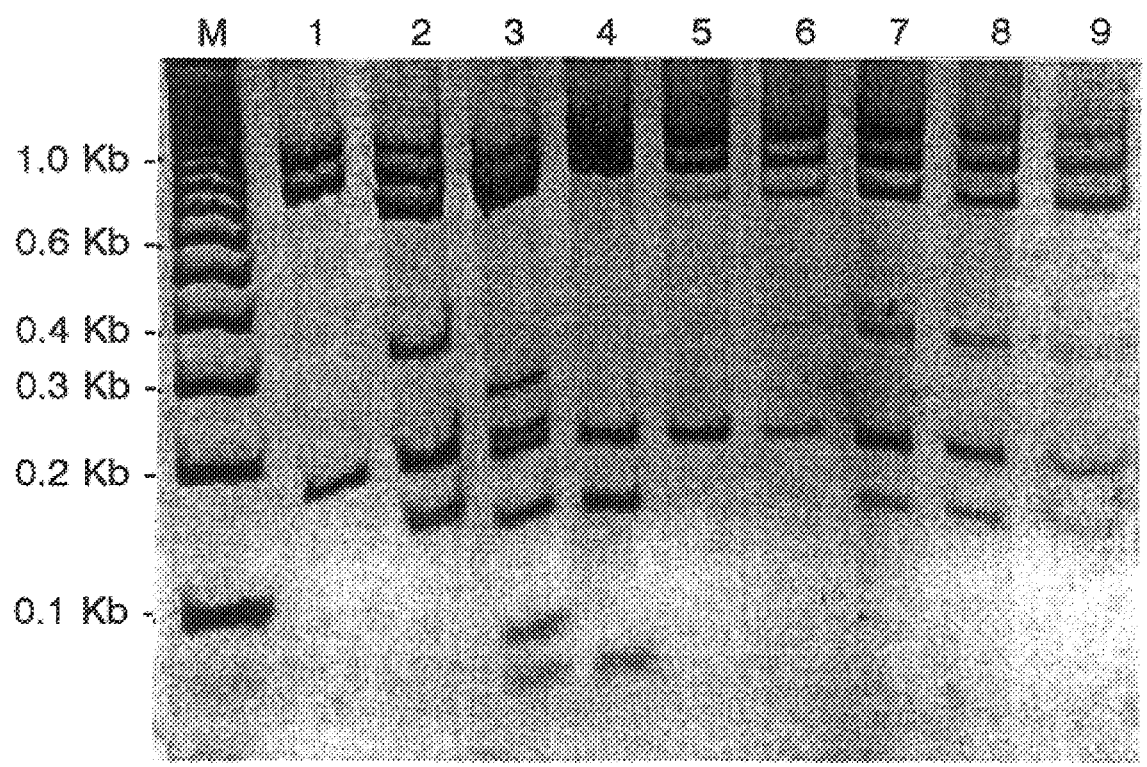
FIG. 9. The Sau3A1 RFLP patterns of the ITS1-5.8S-ITS2 region for P. quinquefolius (American Ginseng), P. ginseng (Oriental ginseng) and their adulterants. Lane M, DNA size marker; lane 1, P. quinquefolius (American Ginseng); lane 2, P. ginseng (Oriental ginseng); lane 3, adulterant M. jalapa; lane 4, adulterant P. acinosa. Lane 5 to 9 represent the RFLP patterns of the mixed samples of American Ginseng and Oriental ginseng in different ratio. Lane 5, American Ginseng and Oriental ginseng in the ratio of 9:1; Lane 6, in the ratio of 7:3; Lane 7, in the ratio of 1:1; Lane 8, in the ratio of 3:7; and Lane 9, in the ration of 1:9. When Compared to American ginseng, Oriental ginseng contains three additional DNA fragments at the size of 0.7 kb, 0.35 kb and 0.17 kb. The 0.35 kb fragment is absent from the two adulterants. On the other hand, in comparison of ginsengs, M. jalapa contains three additional fragment of 0.3 kb, 0.07 kb and 0.05 kb in size, and P. acinosa contains an additional fragment of 0.05 kb in size. The plant DNA were extracted using CTAB method and their rDNA ITS regions were amplified by PCR using the primers specified in FIG. 6. The resultant PCR products were subject to restriction of Sau3A1, fractionated on SDS-PAGE and silver stained.

This invention provides an isolated nucleic acid molecule having the ITS1-5.8S-ITS2 sequence. This invention also provides isolated nucleic acid molecules having the ITS1-5.8S-ITS2 sequence from plant cultivers. It is expected even within the same species, there will be a minor variation between them. Such variation may be up to 1% or less. It is intent of this invention to cover this variation and it is easily appreciated by a person of ordinary skill in the art that the claimed invention work the same with this variation.

This invention provides an isolated nucleic acid molecule having the ITS1-5.8S-ITS2 sequence of P. quinquefolius. In an embodiment, this sequence is as set forth in FIG. 1.

In an embodiment, the ITS1-5.8S-ITS2 sequence is the DNA sequence between the oligonucleotide primers 18d and 28cc.

This invention provides an isolated nucleic acid molecule having the TS1-5.8S-ITS2 sequence of P. ginseng. In an embodiment, the sequence is as set forth in FIG. 2A or B.

This invention provides an isolated nucleic acid molecule having the ITS1-5.8S-ITS2 sequence of P. japonicus. In a perferred embodiment, the sequence is as set forth in FIG. 3.

This invention provides an isolated nucleic acid molecule having the ITS1-5.8S-ITS2 sequence of P. notoginseng. In a perferred embodiment, the sequence is as set forth in FIG. 4.

This invention provides an isolated nucleic acid molecule having the ITS1-5.8S-ITS2 sequence of P. trifolium. In an embodiment, the sequence is as set forth in FIG. 5.

This invention also provides a method for authenticating the identity of herbs comprising the following steps: (a) extracting rDNA from a herb sample with known identity determined by traditional means; (b) amplifying the ITS1-5.8S-ITS2 region of the extracted rDNA using oligonucleotide primers that are conserved across plant kingdom and that flank to the ITS1-5.8S-ITS2 region by polymerase chain reaction; (c) digesting the amplified ITS1-5.8S-ITS2 region with appropriate restriction endonucleases to generate restriction fragments; and (d) separating the restriction fragments resulted from step (c) to generate profiles and comparing these profiles with the known profiles from an authenticated sample with the same identity, wherein similar profiles confirms the identity of the herbal sample.

This invention further provides a method for identifying a herbal material comprising the following steps: (a) extracting rDNA from the herbal material; (b) amplifying the ITS1-5.8S-ITS2 region of the extracted rDNA using oligonucleotide primers that are conserved across plant kingdom and that flank to the ITS1-5.8S-ITS2 region by polymerase chain reaction; (c) digesting the amplified ITS1-5.8S-ITS2 region with appropriate restriction endonucleases to generate restriction fragments; and (d) separating the restriction fragments resulted from step (c) to generate a profile of the herbal material and comparing this profile with known profiles from different herbs, wherein the showing of similar profile with a known herb identifies the herbal material.

This invention provides an isolated nucleic acid molecule having the ITS1-5.8S-ITS2 sequence. In an embodiment, the sequence is from an animal.

This invention also provide a method for authenticating the identity of an animal traditional Chinese medicine comprising the following steps: (a) extracting rDNA from an animal traditional Chinese medicine sample with known identity determined by traditional means; (b) amplifying the ITS1-5.8S-ITS2 region of the extracted rDNA using oligonucleotide primers that are conserved across animal kingdom and that flank to the ITS1-5.8S-ITS2 region by polymerase chain reaction; (c) digesting the amplified ITS1-5.8S-ITS2 region with appropriate restriction endonucleases to generate restriction fragments; and (d) separating the restriction fragments resulted from step (c) to generate profiles and comparing these profiles with the known profiles from an authenticated sample with the same identity, wherein similar profiles confirms the identity of the animal traditional Chinese medicine.

Finally, this invention provides a method for identifying an animal traditional Chinese medicine comprising the following steps: (a) extracting rDNA from the Chinese medicine; (b) amplifying the ITS1-5.8S-ITS2 region of the extracted rDNA using oligonucleotide primers that are conserved across animal kingdom and that flank to the ITS1-5.8S-ITS2 region by polymerase chain reaction; (c) digesting the amplified ITS1-5.8S-ITS2 region with appropriate restriction endonucleases to generate restriction fragments; and (d) separating the restriction fragments resulted from step (c) to generate a profile of the herbal material and comparing this profile with known profiles from different known animal Chinese medicine sample, wherein the showing of similar profile with a known animal sample identifies the animal Chinese medicine.

In order to facilitate an understanding of the following examples, certain frequently occurring methods and/or terms are best described in Sambrook, et al. (Sambrook, et al. (1989)).

This invention will be better understood by reference to the Experimental Details section which follows, but those skilled in the art will readily appreciate that the specific experiments detailed are only illustrative of the invention as described more fully in the claims which follow thereafter.

EXPERIMENTAL DETAILS

Extraction of plant DNA. Dried roots of P. quinquefolius were from Canada, P. ginseng from China; M. jalapa L and P. acinosa Roxb from Hong Kong. The dried samples were rinsed with 70% ethanol and then distilled water to remove surface contaminants. The samples were then ground into fine powder in liquid nitrogen by a mortar and pestle. Powders of P. quinquefolius and P. ginseng were mixed in different proportion of 9:1, 7:3, 1:1, 3:7 and 1:9 in the mixed sampling assay. Ground sample powder was added into 12 vol. of 1×CTAB extraction buffer [50 mM Tris-HCl, pH 8.0, 0.7M NaCl, 10 mM EDTA, 1% cetyl triethylammonium bromide (CTAB), 20 mM 2-mercaptoethanol] and incubated for 30 min at 56° C. with occasional shaking. The CTAB extraction buffer was pre-warmed to 56° C. The mixture was then cooled down to room temperature and extracted with an equal volume of chloroform/isoamyl alcohol (24:1). After centrifugation at 13,000×g for 10 min., the aqueous phase was extracted with 0.1 vol. of 10% CTAB solution. It was then extracted again with an equal volume of chloroform/isoamyl alcohol (24:1). The aqueous phase was collected, and added with an equal volume of 1×CTAB precipitation buffer [50 mM Tris-HCl, pH 8.0, 10 mM EDTA, 1% CTAB]. After standing at room temperature for 1 hour, the solution was centrifuged at 13,000×g for 15 min. The resultant pellet was resuspended in 400 ul 1M NaCl, added with 800 ul of cooled absolute ethanol and stored at −20 C. overnight. The suspension was centrifuged at 13,000×g for 10 min. and the pellet was washed with 70% ethanol twice. It was then dried and resuspended in 50 ul TE buffer [10 mM Tris-HCl, pH 8.0, 1 mM EDTA]. Further purification by CsCl gradient ultracentrifugation is optional.

Amplification of rDNA. The plant rDNA was amplified using a pair of primers 18d and 28cc (Hillis, D. M and Dixon, M. T., 1991, The Quarterly Review of Biology, 66: 411–453), which correspond to the conserved regions of plant 18S and 28S respectively.

18d: CACAC CGCCC GTCGC TCCTA CCGA (SEQ ID NO.10)

28cc: ACTCG CCGTT ACTAG GGGAA (SEQ ID NO.11)

The reaction was performed in a 50 ul mixture containing 1 ng plant DNA, 1×Taq buffer [10 mM Tris-HCl, pH 8.3, 50 mM KCl, 0.001% gelatin], 0.2 mM dNTPs, 1 uM of each primer and 1 unit of Taq polymerase. Reaction mixtures were overlaid with mineral oil and reaction was carried out in a Thermolyne thermocycler. Initial template denaturation was programmed at 94 C., 5 min. It was then subjected to 35 cycles of 94 C. for 1 min.; 60 C. for 1 min.; 72 C. for 2 min., and with a final extension of 72 C. for 10 min. After the reaction, the products were resolved by a 1.4% TBE agarose gel.

Sequencing ITS1-5.8S-ITS2. The ITS1-5.8S-ITS2 region of plant rDNA was sequenced in both strands using a set of primers on the conserved regions of the flanking 18S and 28S rDNA. The sequences of the primers used were as follows (Hillis, D. M and Dixon, M. T., 1991, The Quarterly Review of Biology, 66: 411–453):

18d: CACAC CGCCC GTCGC TCCTA CCGA (SEQ ID NO.12)

5.8c: TTGCG TTCAA AGACT CGATG (SEQ ID NO.13)

5.8d: AACCA TCGAG TCTTT GAACG CA (SEQ ID NO.14)

28cc: ACTCG CCGTT ACTAG GGGAA (SEQ ID NO.15)

SequiThermTM Cycle Sequencing Kit (Epicentre, Madison, Wis.) was used to direct-sequence the PCR-amplified rDNA containing ITS-5.8S-ITS2. The sequencing procedure was done according to the manufacturers's instruction. The products were resolved onto a standard 8% polyacrylamide sequencing gel.

Determination of Restriction Fragment Length Polymorphisms in the ITS1-5.8S-ITS2 region. Plant rDNA amplified using primers 18d and 28cc was purified using Geneclean kit (Bio101, Inc.) and digested with selected restriction endonucleases TaqI, Sau3AI or HinfI. 1.5 ug rDNA was used for each digestion in a volume of 50 ul. For TaqI. a buffer of 100 mM NaCL, 10 mM Tris-HCl, 10 mM MgCl2, 10 mM 2-mercaptoethanol, pH 8.4, supplemented with 100 ug/ml bovine serum albumin was used and the digestion was carried out at 65 C. for 4 hours. For Sau3AI, a buffer of 100 mM NaCl, 10 mM Tris-HCl, 10 mM MgCl2, pH 7.3, supplemented with 100 ug/ml bovine serum albumin was used. For HinfI a buffer of 50 mM NaCl, 10 mM Tris-HCl, 10 mM MgCl2, 1 mM dithiothreitol, pH 7.9 was used. The reaction for both Sau3AI and HinfI was incubated at 37 C. for 4 hours. The products were then purified by phenol: chloroform: isoamyl alcohol (25:24:1) and dissolved in 20 ul distilled water. They were resolved in a 5% PAGE and detected with Bio-Rad silver stain kit (Bio-Rad, Ltd).

ADVANTAGES OF THE INVENTION

The method of authentication of ginsengs described above are expected to be suitable for authentication of other herbal traditional Chinese medicine as well, considering the existence of the conserved DNA sequences flanking to the ITS1-5.8S-ITS2 region in plant kingdom and the variation in the ITS1 and ITS2 regions among different plant species. In comparison to the existing procedures of authentication of traditional Chinese medicine, this invention provides the following advantages:

a. the authentication results are reliable and reproducible, and are not affected by the physical forms and age of the plant samples;

b. it is a method of high sensitivity: microgram sample is sufficient;

c. more than one distinctive profiles with different enzymatic digestion can be produced and that makes the interpretation of results straightforward;

d. the contamination of other biological materials can be detected.

REFERENCE

Hillis, D. M and Dixon, M. T. (1991) Ribosomal DNA: molecular evolution and phylogenic infrrence. *Quar. Rev. Biol.*, 66: 411–453.

Lang, Z., Lou, W S. and But, P P H. (1993) High performance liquid chromatographical analysis of ginsenosides in *Panax ginseng* and *P. notoginseng. J. Clin. Pharm. Sci.,* 2:133–143.

Sambrook, et al. (1989) *Molecular Cloning: A Laboratory Manual.*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 874 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
ACTCGCCGTT ACTAGGGGAA TCCTTGTAAG TTTCTTTTCC TCCGCTTATT GATATGCTTA        60
AACTCAGCGG GTAGTCCCGC TGACCTGGGG TCGCGGTCGG AGCGCACGTC GAGGAGCGCA       120
ACAGGGTCAT GAGAGCTTTT GCTGGCGACG GGTCACCGCA CGACATGAGA AGAGGGCTTT       180
TTACAACCAC CACTTGTCGT GACGTCCATC GCCAAGGACT CGCATTTGGG CCAACCGCGC       240
GGTGAGACAC GGGAGGCCAT TATCCGCCCC TCCGCCTCGA CTCCCGCAAA GGAGTGATGG       300
GTTGGGGGGC GACGCGATGC GTGAACGCCC AGGCAGACGT GCCCTCGGCC TAATGGCTTC       360
GGGCGCAACT TGCGTTCAAA GACTCGATGG TTCACGGGAT TCTGTAATTC ACACCAAGTA       420
TCGCATTTCG CTACGTTCTT CATCGATGCG AGAGCCGAGA TATCCGTTGC CGAGAGTCGT       480
TTGTGTTTTA GAAAGACGCT TCCGCCGCCC GCAAACGGGG GGGACGCGTG CAGTTCAGTT       540
TGATTTCCTT GGCGCATTCC GCGCCGGGGG GTCGTTGTTC GGACGAGAGC CACCCAAGGG       600
TGGTCCCCGA CCATGGGTTT GCAACTTGGG GAGCTTGCGC ACCCCTCGTC CCTCACCCGG       660
TATTGTAACG TGTTCGCGGG TCGTTCTGCT ATGCAGGTTT CGACAATGAT CCTTCCGCAG       720
GTTCACCTAC GGAAACCTTG TTACGACTTC TCCTTCCTCT AAATGATAAG GTTCAGTGGA       780
CTTCTTTCGA CGTCGCGGGC AGCGAACCGC CCACGTCGCC GCAATCCGAA CACTTCACCG       840
GACCATTCAA TCGGTAGGAG CGACGGGCGG TGTG                                  874
```

( 2 ) INFORMATION FOR SEQ ID NO:2:

( i ) SEQUENCE CHARACTERISTICS:
        ( A ) LENGTH: 875 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

```
ACTCGCCGTT ACTAGGGGAA TCCTTGTAAG TTTCTTTTCC TCCGCTTATT GATATGCTTA        60
AACTCAGCGG GTAGTCCCGC TGACCTGGGG TCGCGGTCGG AGCGCACGTC GAGGACGGCG       120
CAACAGGGTC ATGAGAGCTT TTGCTGGCGA CGGGTCACCG CACGACATGA GAAGAGGGCT       180
TTTTACAACC ACCACTTGTC GTGACGTCCA TCGCCAAGGA CTCGCATTTG GGCCAACCGC       240
```

| | | | | | |
|---|---|---|---|---|---|
| GCGGTGAGAC | ACGGGAGGCC | ATTATCCGCC | CCTCCGCCTC | AACTCCCGCA | AGGGAGTGAT | 300
| GGGTTGGGGG | GCGACGCGAT | GCGTGACGCC | CAGGCAGACG | TGCCCTCGGC | CTAATGGCTT | 360
| CGGGCGCAAC | TTGCGTTCAA | AGACTCGATG | GTTCACGGGA | TTCTGCAATT | CACACCAAGT | 420
| ATCGCATTTC | GCTACGTTCT | TCATCGATGC | GAGACGCGAG | ATATCCGTTG | TCGAGAGTCG | 480
| TTTGTGTTTT | AGAAAGACGC | TTCCGCCGCC | CGCAAACGGG | GGGACGCGT | GCAGTTCAGT | 540
| TTGATTTCCT | TGGCGCATTC | CGCGCCGGGG | GGTCGTTGTT | CGGACGAGAT | CCACCCAAGG | 600
| GTGGTCCCCG | ACCATGGGTT | TGCAACTTGG | GGAGCTTGCG | CACCCCTCGT | CCCTCACCCG | 660
| GTATTGTAAC | GTGTTCGCGG | GTCGTTCTGC | TATGCAGGTT | TCGACAATGA | TCCTTCCGCA | 720
| GGTTCACCTA | CGGAAACCTT | GTTACGACTT | CTCCTTCCTC | TAAATGATAA | GGTTCAGTGG | 780
| ACTTCTTTCG | ACGTCGCGGG | CAGCGAACCG | CCCACGTCGC | CGCAATCCGA | ACACTTCACC | 840
| GGACCATTCA | ATCGGTAGGA | GCGACGGGCG | GTGTG | | | 875

(2) INFORMATION FOR SEQ ID NO:3:

(i) SEQUENCE CHARACTERISTICS:
        (A) LENGTH: 875 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

| | | | | | |
|---|---|---|---|---|---|
| ACTCGCCGTT | ACTAGGGGAA | TCCTTGTAAG | TTTCTTTTCC | TCCGCTTATT | GATATGCTTA | 60
| AACTCAGCGG | GTAGTCCCGC | TGACCTGGGG | TCGCGGTCGG | AGCGCACGTC | GAGGACGGCG | 120
| CAACAGGGTC | ATGAGAGCTT | TTGCTGGCGA | CGGGTCACCG | CACGACATGA | GAAGAGGGCT | 180
| TTTTACAACC | ACCACTTGTC | GTGACGTCCA | TCGCCAAGGA | CTCGCATTTG | GCCAACCGC | 240
| GCGGTGAGAC | ACGGGAGGCC | ATTATCCGCC | CCTCCGCCTC | AACTCCCGCA | AGGGAGTGAT | 300
| GGGTTGGGGG | GCGACGCGAT | GCGTGACGCC | CAGGCAGACG | TGCCCTCGGC | CTAATGGCTT | 360
| CGGGCGCAAC | TTGCGTTCAA | AGACTCGATG | GTTCACGGGA | TTCTGCAATT | CACACCAAGT | 420
| ATCGCATTTC | GCTACGTTCT | TCATCGATGC | GAGACGCGAG | ATATCCGTTG | TCGAGAGTCG | 480
| TTTGTGTTTT | AGAAAGACGC | TTCCGCCGCC | CGCAAACGGG | GGGACGCGT | GCAGTTCAGT | 540
| TTGATTTCCT | TGGCGCATTC | CGCGCCGGGG | GGTCGTTGTT | CGGACGAGAT | CCACCCAAGG | 600
| GTGGTCCCCG | ACCATGGGTT | TGCAACTTGG | GGAGCTTGCG | CACCCCTCGT | CCCTCACCCG | 660
| GTATTGTAAC | GTGTTCGCGG | GTCGTTCTGC | TATGCAGGTT | TCGACAATGA | TCCTTCCGCA | 720
| GGTTCACCTA | CGGAAACCTT | GTTACGACTT | CTCCTTCCTC | TAAATGATAA | GGTTCAGTGG | 780
| ACTTCTTTCG | ACGTCGCGGG | CAGCGAACCG | CCCACGTCGC | CGCAATCCGA | ACACTTCACC | 840
| GGACCATTCA | ATCGGTAGGA | GCGACGGGCG | GTGTG | | | 875

(2) INFORMATION FOR SEQ ID NO:4:

(i) SEQUENCE CHARACTERISTICS:
        (A) LENGTH: 870 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

| | | | | | |
|---|---|---|---|---|---|
| ACTCGCCGTT | ACTAGGGGAA | TCCTTGTAAG | TTTCTTTTCC | TCCGCTTATT | GATATGCTTA | 60

| | | | | | | |
|---|---|---|---|---|---|---|
| AACTCAGCGG | GTAGTCCGGC | CTGACCTGGG | GTCGCGGTCG | GAGCGCACGT | CGAGGACGGC | 120 |
| GCAACAGGGT | CATGAGAGCT | TTTGCTGGCG | ACGGGTCACC | GCACGACATG | AGAAGAGGGC | 180 |
| TTTTTACAAC | CACCACTTGT | CGTGACGTCC | ATCGCCAAGG | ACTCGCATTT | GGGCCAACCG | 240 |
| CGCGGTGAGA | CACGGGAGGC | CATTATCCGC | CCCTCCGCCT | CAACTCCCGC | AAGGGAGTGA | 300 |
| TGGGTTGGGG | GGCGACGCGA | TGCGTGACGC | CAGGCAGAC | GTGCCCTCGG | CCTAATGGCT | 360 |
| TCGGGCGCAA | CTTGCGTTCA | AAGACTCGAT | GGTTCACGGG | ATTCTGCAAT | TCACACCAAG | 420 |
| TATCGCATTT | CGCTACGTTC | TTCATCGATG | CGAGAGCCGA | GATATCCGTT | GCCGAGAGTC | 480 |
| GTTTGTGTTT | TAGAAAGACG | CTTCCGCCGC | CCGCAAACGG | GGGGACGCG | TGCAGTTCAG | 540 |
| TTTGATTTCC | TTGGCGCATT | CCGCGCCGGG | GGGTCGTTGT | TCGGACGAGA | TCCACCCAAG | 600 |
| GGTGGTCCCC | GACCATGGGT | TTGCAACTTG | GGGAGCTTGC | GCACCCCTCG | TCCCTCACCC | 660 |
| GGTATTGTAA | CGTGTTCGCG | GTCGTTCTG | CTATGCAGGT | TTCGACAATG | ATCCTTCCGC | 720 |
| AGGTTCACCT | ACGGAAACCT | TGTTACGACT | CTCCTTCCT | CTAAATGATA | AGGTTCAGTG | 780 |
| GACTTCTTTC | GACGTCGCGA | GCAGCGAACC | GCCCACGTCG | CCGCAATCCG | AACACTTCAC | 840 |
| CGGACCATTC | AATCGGTAGG | AGCGACGGGG | | | | 870 |

(2) INFORMATION FOR SEQ ID NO:5:

(i) SEQUENCE CHARACTERISTICS:
        (A) LENGTH: 875 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

| | | | | | | |
|---|---|---|---|---|---|---|
| ACTCGCCGTT | ACTAGGGGAA | TCCTTGTAAG | TTTCTTTTCC | TCCGCTTATT | GATATGCTTA | 60 |
| AACTCAGCGG | GTAGTCCGC | CTGACCTGGG | GTCGCGGTCG | GAGCGCACGT | CGAGGACGGC | 120 |
| GCAACAGGGT | CATGAGAGCT | TTTGTTGGCG | AAGGGTCACC | GCACGACATG | AGAAGAGGGC | 180 |
| TTTTTACAAC | CACCACTTGT | CGTGACGTCC | ATCGCCAAGG | ACTCGCATTT | GGGCCAACCG | 240 |
| CACGGTGAGA | CACGGGAGGC | CAATATCCGC | CCCTCCGCCT | CGACTCCCGC | AAGGGAGTGA | 300 |
| TGGGTTGGGG | GGCGACGCGA | TGCGTGAACG | CCCAGGCAGA | CGTGCCCTCG | GCCTAATGGC | 360 |
| TTAGGGCGCA | ACTTGCGTTC | AAAGACTCGA | TGGTTCACGG | GATTCTGCAA | TTCACACCAA | 420 |
| GTATCGCATT | TCGCTACGTT | CTTCATCGAT | GCGAGAGCCG | AGATATCCGT | TGCCGAGAGT | 480 |
| CGTTTGTGTT | TTAGAAAGAC | GCTTCCGCCG | CCCGCAAATG | GGGGGACGC | GTGCAGTTCA | 540 |
| GTTTGATTTC | CTTGGCACAT | TCCGCGCCGG | GGGGTCGTTG | TTCGGACGAG | ATCCACCAAG | 600 |
| GGTGTCCCCG | ACCATGGGTT | TGCAACTTGG | GGAGCTTGCG | CACGCCTCGT | CCCTCACCCG | 660 |
| GTATTGTAAC | GTGTTCACGG | GTCGTTCTGC | TATGCAGGTT | TCGACAATGA | TCCTTCCGCA | 720 |
| GGTTCACCTA | CGGAAACCTT | GTTACGACTT | CTCCTTCCTC | TAAATGATAA | GGTTCAGTGG | 780 |
| ACTTCTTTCG | ACGTCGCGGG | CAGCGAACCG | CCCACGTCGC | CGCAATCCGA | ACACTTCACC | 840 |
| GGACCATTCA | ATCGGTAGGA | GCGACGGGCG | GTGTG | | | 875 |

(2) INFORMATION FOR SEQ ID NO:6:

(i) SEQUENCE CHARACTERISTICS:
        (A) LENGTH: 876 base pairs
        (B) TYPE: nucleic acid
        (C) STRANDEDNESS: single
        (D) TOPOLOGY: linear (  i i  ) MOLECULE TYPE: DNA (  x i  ) SEQUENCE DESCRIPTION: SEQ ID NO:6:

| | | | | | |
|---|---|---|---|---|---|
| ACTCGCCGTT | ACTAGGGGAA | TCCTTGTAAG | TTTCTTTTCC | TCCGCTTATT | GATATGCTTA | 60 |
| AACTCAGCGG | GTAGTCCCGC | TGACCTGGGG | TCGCGGTCGG | AGCGCACGTC | GAGGACGGCG | 120 |
| CAACAGGGTC | ATGAGAGCTT | TTGCTGGCGA | CGGGTCACCG | CACGACATGA | AAGAGGGCT | 180 |
| TTTTACAACC | ACCACTTGTC | GTGACGTCCA | TCGCCAAGGA | CTCGCATTTG | GGCCAACCGC | 240 |
| GCGGTGAGAC | ACGGGAGGCC | ATTATCCGCC | CCTCCGCCTC | GACTCCCGCA | AAGGAGTGAT | 300 |
| GGGTTGGGGG | GCGACGCGAT | GCGTGAACGC | CCAGGCAGAC | GTGCCCTCGG | CCTAATGGCT | 360 |
| TCGGGCGCAA | CTTGCGTTCA | AAGACTCGAT | GATTCACGGG | ATTCTGCAAT | TCACACCAAG | 420 |
| TATCGCATTT | CGCTACGTTC | TTCATCGATG | CGAGAGCCGA | GATATCCGTT | GCCGAGAGTC | 480 |
| GTTTGTGTTT | TAGAAAGACG | CTTCCGCCGC | CCGCAAACGG | GGGGACGCG | TGCAGTTCAG | 540 |
| TTTGATTTCC | TTGGCGCATT | CCGCGCCGGG | GGGTCGTTGT | TCGGACGAGA | GCCACCCAAG | 600 |
| GGTGGTCCCC | GACCATGGGT | TTGCAACTTG | GGGAGCTTGC | GCACCCCTCG | TCCCTCACCC | 660 |
| GGTATTGTAA | CGTGTTCGCG | GGTCGTTCTG | CTATGCAGGT | TTCGACAATG | ATCCTTCCGC | 720 |
| AGGTTCACCT | ACGGAAACCT | TGTTACGACT | TCTCCTTCCT | CTAAATGATA | AGGTTCAGTG | 780 |
| GACTTCTTTC | GACGTCGCAG | GCAGCGAACC | GCCCACGTCG | CCGCAATCCG | AACACTTCAC | 840 |
| CGGACCATTC | AATCGGTAGG | AGCGACGGGC | GGTGTG | | | 876 |

(  2  ) INFORMATION FOR SEQ ID NO:7:

(  i  ) SEQUENCE CHARACTERISTICS:
        ( A ) LENGTH: 875 base pairs
        ( B ) TYPE: nucleic acid
        ( C ) STRANDEDNESS: single
        ( D ) TOPOLOGY: linear (  i i  ) MOLECULE TYPE: DNA (  x i  ) SEQUENCE DESCRIPTION: SEQ ID NO:7:

| | | | | | |
|---|---|---|---|---|---|
| ACTCGCCGTT | ACTAGGGGAA | TCCTTGTAAG | TTTCTTTTCC | TCCGCTTATT | GATATGCTTA | 60 |
| AACTCAGCGG | GTAGTCCCGC | CTGACCTGGG | GTCGCGGTCG | GAGCGCGCGT | CGGGGACGGC | 120 |
| GCAACAGGGT | CGTGAGAGCC | TTTGCCGGCG | ACGGGTCACC | GCACGACTTG | AGAAGAGGGC | 180 |
| TTTTTACAAC | CACCACTTGT | CGTGACGTCC | GTCGCCGAGG | ACTCGCATTT | GGGCCAACCG | 240 |
| CGCGGTTAGA | CACGGGAGGC | CAATATCCGC | CCCTCCGCCT | CGACTCCCGT | AAGGGAGTGA | 300 |
| TGGGTTGGGG | GGCGACGCGA | TGCGTGACGC | CCAGGCAGAC | GTGCCCTCGG | CCTAATGGCT | 360 |
| TAGGGCGCAA | CTTGCGTTCA | AAGACTCGAT | GGTTCACGGG | ATTCTGCAAT | TCACACCAAG | 420 |
| TATCGCATTT | CGCTACGTTC | TTCATCGATG | CGAGAGCCGA | GATATCCGTT | GCCGAGAGTC | 480 |
| GTTTGTGTTT | TAGAAAGACG | CTTCCGCCGC | CCGCAAACGG | GGGGACGCG | TGCAGTTCAG | 540 |
| TTTGATTTCC | TTGGCGCATT | CCGCGCCGGG | GGGTCGTTGT | TCGGACGGGG | AGCACCCGGG | 600 |
| GGCGGCCCCC | GACCATGGGT | TCGGAACTTG | GGGGGCTTGC | GCACCCTTCG | TCCCTCACCC | 660 |
| GGTGTTGAAA | CGTGTTCGCG | GGTCGTTCTG | CTGTGCAGGT | TTCGACAATG | ATCCTTCCGC | 720 |
| AGGTTCACCT | ACGGAAACCT | TGTTACGACT | TCTCCTTCCT | CTAAATGATA | AGGTTCAGTG | 780 |
| GACTTCTTTC | GACGTCGCGG | CAGCGAACCG | CCCACGTCGC | CGCAATCCGA | ACACTTCACC | 840 |
| GGACCATTCA | ATCGGTAGGA | GCGACGGGCG | GTGTG | | | 875 |

(  2  ) INFORMATION FOR SEQ ID NO:8:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:8:

AGCCATCCTC GCTGCCCGCC ACAC 24

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:9:

ACTCGCCGTT ACTAGGGGAA 20

(2) INFORMATION FOR SEQ ID NO:10:

(i) SEQUENCE CHARACTERISTICS:
(A) LENGTH: 24 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:10:

CACACCGCCC GTCGCTCCTA CCGA 24

(2) INFORMATION FOR SEQ ID NO:11:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:11:

ACTCGCCGTT ACTAGGGGAA 20

(2) INFORMATION FOR SEQ ID NO:12:

(i) SEQUENCE CHARACTERISTICS:
(A) LENGTH: 24 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:12:

CACACCGCCC GTCGCTCCTA CCGA 24

(2) INFORMATION FOR SEQ ID NO:13:

(i) SEQUENCE CHARACTERISTICS:
(A) LENGTH: 20 base pairs
(B) TYPE: nucleic acid
(C) STRANDEDNESS: double
(D) TOPOLOGY: linear (i i) MOLECULE TYPE: DNA (genomic)

(x i) SEQUENCE DESCRIPTION: SEQ ID NO:13:

TTGCGTTCAA AGACTCGATG                                                           20

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:14:

AACCATCGAG TCTTTGAACG CA                                                        22

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:15:

ACTCGCCGTT ACTAGGGGAA                                                           20

What is claimed is:

1. A method for determining whether a given herbal material is that of *Panax quinquefolius, Panax ginseng, Panax japonicus, Panax notoginseng*, or *Panax trifolium*, wherein said method comprises:
   a) extracting rDNA from the herbal material;
   b) amplifying an ITS1-5.8S-ITS2 region of the extracted rDNA using oligonucleotide primers whose nucleotide residue sequence is conserved across the plant kingdom and which flank the ITS1-5.8S-ITS2 region of *Panax quinquefolius, Panax ginseng, Panax japonicus, Panax notoginseng*, or *Panax trifolium;*
   c) digesting the amplified nucleic acid with a restriction endonuclease so to generate restriction fragments;
   d) separating the restriction fragments resulted from step c) to generate a restriction fragment length profile; and
   e) comparing this restriction fragment profile with known restriction fragment length profiles of herbs thereby determining if the herbal material is that of either *Panax quinquefolius, Panax ginseng, Panax japonicus, Panax notoginseng*, or *Panax trifolium*, or whether the herbal material is from an entirely different source.

2. The method of claim 1 wherein said extracted rDNA comprises a nucleic acid selected from the group consisting of SEQ ID NO:1, SEQ ID NO:3, SEQ ID NO:4, SEQ ID NO:5, SEQ ID NO:6, and SEQ ID NO:7.

3. The method of claim 2 wherein said extracted rDNA comprises SEQ ID NO:1.

4. The method of claim 2 wherein said extracted rDNA comprises SEQ ID NO:3.

5. The method of claim 2 wherein said extracted rDNA comprises SEQ ID NO:4.

6. The method of claim 2 wherein said extracted rDNA comprises SEQ ID NO:5.

7. The method of claim 2 wherein said extracted rDNA comprises SEQ ID NO:6.

8. The method of claim 2 wherein said extracted rDNA comprises SEQ ID NO:7.

9. An isolated nucleic acid consisting of SEQ ID NO:1.
10. An isolated nucleic acid consisting of SEQ ID NO:4.
11. An isolated nucleic acid consisting of SEQ ID NO:5.
12. An isolated nucleic acid consisting of SEQ ID NO:6.
13. An isolated nucleic acid consisting of SEQ ID NO:7.

* * * * *

UNITED STATES PATENT AND TRADEMARK OFFICE
CERTIFICATE OF CORRECTION

PATENT NO. : 5,876,977  
DATED : March 2, 1999  
INVENTOR(S) : Jun Wang, et al

Page 1 of 8

It is certified that error appears in the above-identified patent and that said Letters Patent is hereby corrected as shown below:

In column 2, line 20, italic font "Panax".

In column 2, lines 51-52, delete "(SEQ ID NO.2)" and insert --(SEQ ID NO.1)--.

In column 3, line 1, italic font "Hin"fl.

In column 3, line 20, italic font "Hin"fl.

In column 3, line 22, italic font "Taq"1.

In column 3, line 40, italic font "Taq"1.

In column 3, line 42, italic font "Sau"3A1.

In column 3, line 63, italic font "Sau"3A1.

In column 6, line 20, "NO. 12)" should read --NO. 10)--.

In column 6, line 24, delete "(SEQ ID NO. 15)" and insert --(SEQ ID NO. 11)--.

In column 6, line 35, italic font "Taq"I, and italic font "Sau"3AI, and italic font "Hin"fI.

In column 6, line 36, italic font "Taq"I.

Column 6, line 40, italic font "Sau3"AI.

UNITED STATES PATENT AND TRADEMARK OFFICE
CERTIFICATE OF CORRECTION

PATENT NO. : 5,876,977
DATED : March 2, 1999
INVENTOR(S) : Jun Wang, et al

It is certified that error appears in the above-identified patent and that said Letters Patent is hereby corrected as shown below:

Column 6, line 43, italic font "Hin"fI.

Column 6, line 45, italic font "Sau"3AI, and italic font "Hin"fI.

In the Abstract, line 3, delete "is described".

In column 1, line 16, delete "cicumscribed" and insert --practiced by--.

In column 1, line 18, delete "has" and insert --have--.

In column 1, line 29, delete "which recorded American ginseng".

In column 1, line 33, delete "treaties" and insert --treatises--.

In column 1, line 40, delete "this" and insert --such--.

In column 2, line 9, delete "more expensive" and insert --higher--.

In column 2, line 11, delete "wild-spread" and insert --wide-spread--.

UNITED STATES PATENT AND TRADEMARK OFFICE
CERTIFICATE OF CORRECTION

PATENT NO. : 5,876,977  
DATED : March 2, 1999  
INVENTOR(S) : Jun Wang, et al

It is certified that error appears in the above-identified patent and that said Letters Patent is hereby corrected as shown below:

In column 2, line 16, delete "The" and insert --Pharmacologically, the--.

In column 2, line 40, delete "was" at the second instance and insert --were--.

In column 2, lines 54, delete "sequnece" and insert --sequence--.

In column 2, line 63, after (SEQ ID NO.7)." delete "5'" and insert --3'--.

In column 2, line 64, delete "3'" (each occurrence), and insert --5'".

In column 2, line 64, delete "5'" and insert --3--.

In column 3, line 6, delete "Lane 5 to 9" and insert --Lanes 5 to 9--.

In column 3, line 11, delete "ration" and insert --ratio--.

In column 3, line 12, after "0.06 kb", insert --are--.

In column 3, line 13, delete "ginsen" and insert --ginseng--.

In column 3, line 13, after "0.17 kb", insert --is--.

In column 3, line 21, delete "SDS-PAGE" and insert --PAGE--

UNITED STATES PATENT AND TRADEMARK OFFICE
CERTIFICATE OF CORRECTION

PATENT NO. : 5,876,977
DATED : March 2, 1999
INVENTOR(S) : Jun Wang, et al

It is certified that error appears in the above-identified patent and that said Letters Patent is hereby corrected as shown below:

In column 3, line 34, delete "adulternats" and insert adulterants--.

In column 3, line 35, delete "contains" and insert --contain--.

In column 3, line 53, delete "Compared" and insert --compared--.

In column 4, line 2, delete "cultivers" and insert --cultivars--.

In column 4, line 7, delete "work" and insert --works--.

In column 4, line 15, delete "TS1-5.8S-ITS2" and insert --ITS1-5.8S-ITS2--.

In Column 4, line 20, delete "perferred" and insert --preferred--.

UNITED STATES PATENT AND TRADEMARK OFFICE
CERTIFICATE OF CORRECTION

PATENT NO. : 5,876,977  
DATED : March 2, 1999  
INVENTOR(S) : Jun Wang, et al

Page 5 of 8

It is certified that error appears in the above-identified patent and that said Letters Patent is hereby corrected as shown below:

In column 4, line 23, delete "perferred" and insert --preferred--.

In column 4, line 40, delete "confirms" and insert --confirm--.

In column 5, line 25, delete "(1989))." and insert --1989).--.

In column 5, line 32, underline "Extraction of plant DNA."

In column 5, line 55, delete "[" and "]".

In column 5, line 62, delete "[".

In column 5, line 63, delete "]".

In column 5, line 66, underline "Amplification of rDNA."

In column 6, line 3, italic font "Taq".

In column 6, line 5, italic font "Taq".

In column 6, line 13, underline "Sequencing ITS1-5.8S-ITS2."

In column 6, lines 31-32, underline "Determination of Restriction Fragment Length Polymorphisms in the ITS1-5.8S-ITS2 region."

In column 6, line 37, delete "MgCl2" and insert --$MgCl_2$--.

In column 6, line 40, delete "65 C." and insert --65°C--.

UNITED STATES PATENT AND TRADEMARK OFFICE
CERTIFICATE OF CORRECTION

PATENT NO. : 5,876,977
DATED : March 2, 1999
INVENTOR(S) : Jun Wang, et al

It is certified that error appears in the above-identified patent and that said Letters Patent is hereby corrected as shown below:

In column 6, line 41, delete "MgCl2" and insert --$MgCl_2$--.

In column 6, line 54, delete "are" and insert --is--.

In column 13, last line, delete "(2) INFORMATION FOR SEQ ID NO:8:".

In columns 15-16, delete the following Sequence Listing from page:
"(2) INFORMATION FOR SEQ ID NO:8:
    (i) SEQUENCE CHARACTERISTICS:
        (A) LENGTH: 24 base pairs
        (B) TYPE: nucleic acid
        (C) STRANDEDNESS: single
        (D) TOPOLOGY: linear
   (ii) MOLECULE TYPE: DNA
   (xi) SEQUENCE DESCRIPTION: SEQ ID NO:8:
      AGCCATCCTC GCTGCCCGCC ACAC        24"

In columns 15-16, delete the following Sequence Listing from page:
"(2) INFORMATION FOR SEQ ID NO:9:
    (i) SEQUENCE CHARACTERISTICS:
        (A) LENGTH: 20 base pairs
        (B) TYPE: nucleic acid
        (C) STRANDEDNESS: single
        (D) TOPOLOGY: linear
   (ii) MOLECULE TYPE: DNA
   (xi) SEQUENCE DESCRIPTION: SEQ ID NO:9:
      ACTCGCCGTT ACTAGGGGAA        20"

UNITED STATES PATENT AND TRADEMARK OFFICE
CERTIFICATE OF CORRECTION

PATENT NO. : 5,876,977
DATED : March 2, 1999
INVENTOR(S) : Jun Wang, et al

It is certified that error appears in the above-identified patent and that said Letters Patent is hereby corrected as shown below:

```
In columns 15-16, delete the following Sequence Listing
from page:
"(2) INFORMATION FOR SEQ ID NO:12:
      (i)  SEQUENCE CHARACTERISTICS:
           (A) LENGTH: 24 base pairs
           (B) TYPE: nucleic acid
           (C) STRANDEDNESS: double
           (D) TOPOLOGY: linear
     (ii)  MOLECULE TYPE: DNA (genomic)
     (xi)  SEQUENCE DESCRIPTION: SEQ ID NO:12:
           CACACCGCCC GTCGCTCCTA CCGA                            24"
```

UNITED STATES PATENT AND TRADEMARK OFFICE
CERTIFICATE OF CORRECTION

PATENT NO.  : 5,876,977
DATED       : March 2, 1999
INVENTOR(S) : Jun Wang, et al It is certified that error appears in the above-identified patent and that said Letters Patent is hereby corrected as shown below:

```
In columns 17-18, delete the following Sequence Listing
from page:
"(2) INFORMATION FOR SEQ ID NO:15:
     (i)  SEQUENCE CHARACTERISTICS:
          (A) LENGTH: 20 base pairs
          (B) TYPE: nucleic acid
          (C) STRANDEDNESS: double
          (D) TOPOLOGY: linear
     (ii) MOLECULE TYPE: DNA (genomic)
     (xi) SEQUENCE DESCRIPTION: SEQ ID NO:15:
          ACTCGCCGTT ACTAGGGGAA                               20"
```

Signed and Sealed this

Seventeenth Day of October, 2000

Attest:

Q. TODD DICKINSON

*Attesting Officer*           *Director of Patents and Trademarks*